US012765941B1

(12) United States Patent
Lischinsky

(10) Patent No.: US 12,765,941 B1
(45) Date of Patent: Oct. 20, 2026

(54) SYSTEMS AND METHODS FOR CLASSIFYING AND AMELIORATION OF ADVERSE SIDE EFFECTS ASSOCIATED WITH SUB-CUTANEOUS REGIONS EXHIBITING IMPEDANCE THAT IS DIFFERENT THAN THAT OF ADJECENT TISSUE

(71) Applicant: OHH-MED MEDICAL LTD, Tiberias (IL)

(72) Inventor: Daniel Lischinsky, Ramat Yishai (IL)

(73) Assignee: OHH-MED Medical LTD, Tiberias (IL)

( * ) Notice: Subject to any disclaimer, the term of this patent is extended or adjusted under 35 U.S.C. 154(b) by 0 days.

(21) Appl. No.: 19/305,859

(22) Filed: Aug. 21, 2025

(51) Int. Cl.
*A61B 18/14* (2006.01)
*A61B 5/00* (2006.01)
*A61B 5/053* (2021.01)
*A61B 18/12* (2006.01)
*A61B 18/00* (2006.01)

(52) U.S. Cl.
CPC .......... *A61B 18/1477* (2013.01); *A61B 5/053* (2013.01); *A61B 5/6848* (2013.01); *A61B 5/6867* (2013.01); *A61B 18/1206* (2013.01); *A61B 2018/00875* (2013.01)

(58) Field of Classification Search
CPC . A61B 18/1477; A61B 18/1206; A61B 5/053; A61B 5/6848; A61B 5/6867; A61B 2018/00875
See application file for complete search history.

(56) References Cited

U.S. PATENT DOCUMENTS 11,523,863 B2 12/2022 Ko et al.
2021/0370082 A1 12/2021 Boll et al.

*Primary Examiner* — Joseph M Dietrich

(74) *Attorney, Agent, or Firm* — Guy Levi; The IP Law Firm of Guy Levi, LLC

(57) ABSTRACT

The disclosure relates to devices, systems, sub-systems, and methods for ameliorating adverse side effects associated with a sub-cutaneous region exhibiting impedance that is different than the surrounding tissue and/or organ. More specifically, the disclosure relates to the use of needles equipped with electric impedance sensing and energy discharge capabilities for diagnosing the presence of, and disrupting sub-cutaneous region exhibiting impedance that is different than the surrounding tissue and/or organ, such as, for example focal tunical fibrosis (or plaque), lipomas, and abscesses.

24 Claims, 5 Drawing Sheets

SYSTEMS AND METHODS FOR CLASSIFYING AND AMELIORATION OF ADVERSE SIDE EFFECTS ASSOCIATED WITH SUB-CUTANEOUS REGIONS EXHIBITING IMPEDANCE THAT IS DIFFERENT THAN THAT OF ADJECENT TISSUE

BACKGROUND

The disclosure is directed to devices and methods for ameliorating adverse side effects associated with a sub-cutaneous region exhibiting impedance that is different than the surrounding tissue and/or organ. More specifically, the disclosure is directed to the use of needles equipped with electric impedance sensing and energy discharge capabilities for diagnosing the presence of, and disrupting sub-cutaneous region exhibiting impedance that is different than the surrounding tissue and/or organ, such as, for example focal tunical fibrosis (or plaque), lipomas, and abscesses.

Peyronie's disease (PD) progression is typically classified into acute and chronic phases, with distinct diagnostic and therapeutic considerations for each stage. During the acute phase (typically lasting 6-18 months), patients experience dynamic changes such as penile pain, evolving curvature, and plaque formation due to active inflammation and fibroblast proliferation. Classification in this phase relies on clinical stability criteria, namely resolution of pain and no curvature progression for ≥3-6 months, supported by biomarkers like neutrophil-to-lymphocyte ratio (NLR) and platelet-to-lymphocyte ratio (PLR). Treatment during this phase emphasizes anti-inflammatory agents (e.g., intralesional collagenase *Clostridium histolyticum*/CCH), traction therapy, and oral antioxidants, though evidence for systemic therapies remains limited.

The chronic phase is characterized by stabilized plaques, often with calcification, and absence of pain. Typically, this phase is broadly defined as ≥3-6 months of symptom stability. A more recent classification system (e.g., PTNM, 2024) introduces a more granular subcategorizations for chronic PD: P (PD subtype): classified as: Classical (Cl), calcifying (Ca), progressive (P), relapsing/remitting (R), or undifferentiated (U). T (trauma history): classified as Absent (0) or present (1), while N (non-PD etiology): is classified as Congenital (C), maturational (M), or undifferentiated (U), with M (disease activity): being classified as Stable (0) or active (1). For example, a "PC1T1N0M0" designation indicates stable classical PD with prior trauma. This system acknowledges heterogeneity in chronic PD, such as calcified plaques requiring different surgical approaches (e.g., plaque incision/excision with grafting) compared to non-calcified cases. Stable phase definitions now vary by subtype: Classical: ≥3 months stability, Calcifying/progressive/trauma-induced: ≥12 months since onset+≥3 months stability or ≥6 months stability.

Despite these advancements, no standardized alignment exists between PTNM subtypes and specific treatment protocols. Current guidelines recommend surgical intervention (plication, grafting, or prosthesis implantation) based on general stability criteria rather than subclassifications or severity of the plaque. For instance, calcifying plaques may necessitate more complex grafting procedures, but this is surgeon-dependent rather than protocol-driven. Similarly, relapsing/remitting subtypes lack tailored algorithms, with management often mirroring classical PD approaches.

Ameliorating adverse effects associate with Peyronie's disease has historically been challenging due to the nature of the fibrous plaque and the delicate structure of the penile tissue. As noted, there are several treatment options available, albeit each with its own set of benefits and drawbacks. Non-invasive treatments include oral medications, and external devices; with more invasive methods including intralesional injections, and surgical interventions.

Intralesional injections, which involve the direct administration of medication into the penile plaque (in other words, the focal tunical fibrosis (FTF)). Common agents injected during e.g., the acute stage of the disease, can include verapamil, interferon-alpha-2b, and collagenase *Clostridium histolyticum* (XIAFLEX®). While effective, XIAFLEX® has common adverse side effects including pain, bruising, swelling, and skin tears, as well as serious risks like corporal rupture and flexor tendon ruptures.

External devices, such as penile traction therapy and vacuum erection devices, are also non-invasive options that aim to stretch and remodel the penile tissue. Penile traction therapy involves wearing a device that applies gentle, continuous traction to the penis, while vacuum erection devices create a vacuum to draw blood into the penis, followed by the application of a constriction ring to maintain the erection. These methods can be effective, particularly when used in combination with other treatments, but they require strict regimen adherence and can be cumbersome and uncomfortable, especially in circumstances of chronic PD, with stable deformation present.

Surgical interventions are typically reserved for cases of Peyronie's disease that are recalcitrant or refractive to non-invasive treatments. Surgical options include plication techniques, plaque incision or excision with grafting, and penile prosthesis implantation. While surgery can provide immediate and significant improvement in penile curvature and sexual function, it carries risks such as infection, penile shortening, sensory changes, and recurrence of curvature.

Accordingly, since current practice remains anchored in phase-agnostic factors like curvature severity, erectile function, and patient preference, there is a need for more effective approaches to address the various stages of the disease capable of providing reliable and long-lasting results with minimal side effects. Innovative approaches that diagnose the severity of, and target the underlying fibrotic tissue while preserving the integrity of the surrounding penile tissue would be highly beneficial for improving the management and long-term outcomes of this condition.

Other circumstances where neoplastic growth is associated with adverse side effects, is in the case of lipomas, referring to a benign tumor composed primarily of mature adipocytes, typically arising in the subcutaneous tissues but occasionally occurring in deeper locations such as intramuscular or intra-abdominal spaces. Large lipomas (generally referring to lesions larger than 5 cm), raise (albeit rare) concern for possible liposarcoma, while also presenting technical and functional management challenges. Large lipomas may become symptomatic due to mass effect, disfigurement (both when present and when removed), interference with movement, or pressure effects on overlying skin or underlying neurovascular structures.

Treatment of lipomas remains primarily surgical, with simple excision being the gold standard, particularly for larger lesions. However, there are notable shortcomings associated with current treatment modalities for lipomas, and especially, large lipomas. Surgical excision of lesions can result in significant scarring, wound-healing complications, hematoma or seroma formation, and, depending on location, risk of injury to surrounding neurovascular bundles. Additionally, recurrence rates, although generally low, can be higher for lesions that are not completely excised, or those lesions in anatomically complex sites. For example, liposuction has been used as a minimally invasive alternative for larger subcutaneous lipomas, typically resulting in smaller scars and more rapid recovery, but this technique is associated with a higher local recurrence risk due to possible residual tissue. Additionally, large lipomas may have non-encapsulated or multilobulated extensions, making identification and complete removal challenging and increasing the chance of recurrence. Furthermore, non-surgical approaches, such as injectable lipolytic agents, have shown only very limited effectiveness and are not considered standard of care for large lipomas. Consequently, currently there is a lack of robust, evidence-based data supporting their use, particularly for large or deeply situated tumors.

Likewise the presence of abscesses (referring to the localized collection of pus that develops within the dermis, subcutaneous tissue, or deeper structures in response to tissue infection and resultant acute inflammation), can present additional challenge for treatment of adverse side effects. These generally present as encapsulated by a wall of granulation tissue and comprises a mix of live and dead neutrophils, bacteria, cellular debris, and proteins.

Despite the prevalence presentation of abscesses, several treatment shortcomings persist, especially in the management of complicated, recurrent, large, or atypical abscesses. The typical therapy for uncomplicated abscesses is incision and drainage (I&D), which, although generally effective for superficial lesions, can sometimes be insufficient for deeper or multiloculated abscesses, potentially requiring imaging guidance, and more extensive exploration, or even surgical intervention. Antibiotics are typically adjunctive and, while beneficial in cases of cellulitis or systemic involvement, or for abscesses in high-risk patients, have otherwise limited utility because they may not actually penetrate the abscess cavity. The overuse of antibiotics, particularly in the absence of systemic features, contributes to antimicrobial resistance and unnecessary drug exposure, yet their omission in borderline cases may place certain patients at increased risk of inadequate treatment. In addition, unresolved issues remain regarding the optimal use of imaging for diagnosis and guidance, particularly distinguishing abscesses from cellulitis or deep-seated non-infectious lesions. The role of emerging minimally invasive modalities—such as ultrasound-guided drainage, needle aspiration alone, or adjunctive therapies like negative pressure wound therapy—have shown promise but require further research to establish their consistency and superiority compared to traditional techniques.

These and other issues are addressed by providing novel devices and methods for ameliorating adverse side effects associated with a sub-cutaneous region exhibiting impedance that is different than the surrounding tissue and/or organ, such as focal tunical fibrosis, lipomas abscesses and the like.

SUMMARY

In an exemplary implementation, provided herein is a system for use in a procedure for ameliorating adverse side effects associated with a sub-cutaneous region exhibiting impedance that is different than the surrounding tissue and/or organ in a subject in need thereof, by applying RF energy thereto, the device comprising: a wand having a at least one needle adapted, sized and configured to penetrate a surface of a skin region of the subject; a radio frequency (RF) generator, operable to deliver RF energy to the sub-cutaneous region exhibiting impedance that is different than the surrounding tissue and/or organ via the at least one needle; and a central processing module (CPM), in communication with the wand, and the RF generator operable to control: depth of sub-cutaneous penetration of the at least one needle; intensity of an RF energy delivery by the RF generator, to the sub-cutaneous region exhibiting impedance that is higher than the surrounding tissue and/or organ; and optionally, polarity of the at least one needle penetrated.

In another exemplary implementation, provided is a device for use in a procedure for ameliorating adverse side effects of a focal tunical fibrosis in a patient in need thereof, by applying RF energy thereto, the device comprising: a wand having a plurality of needles adapted to penetrate a surface of a user's skin; a radio frequency (RF) generator, arranged to deliver RF energy to an area beneath the penetrated skin via at least one needle of the plurality of needles; and a central processing module (CPM), in communication with the wand, and the RF generator operable to control: the depth of penetration of each needle of the plurality of needles; the polarity of each needle of the plurality of needles penetrated into the area beneath the penetrated skin; and an RF energy delivery by the RF generator to the area beneath the penetrated skin.

In yet another exemplary implementation, provided herein is a method for ameliorating adverse effects associated with a sub-cutaneous region exhibiting impedance that is different than the surrounding tissue and/or organ, in a subject in need thereof, implemented in a device comprising a wand having a plurality of needles adapted to penetrate a surface of a user's skin, a radio frequency (RF) generator, arranged to deliver RF energy to an area beneath the penetrated skin via at least one needle of the plurality of needles, and a central processing module (CPM), in communication with the wand, and the RF generator operable to control: the depth of penetration of each needle of the plurality of needles, an intensity of RF energy delivery by the RF generator to the area beneath the penetrated skin, and optionally, the polarity of each needle of the plurality of needles penetrated into the area beneath the penetrated skin, the method comprising: penetrating the sub-cutaneous region exhibiting impedance that is different than the surrounding tissue and/or organ with the plurality of needles; delivering radiofrequency (RF) energy via at least one needle to the sub-cutaneous region; controlling, via the central processing module (CPM): penetration depth of each needle; RF energy delivery parameters to the sub-cutaneous region; and optionally, polarity assignment of each needle.

In an exemplary implementation, provided herein is a method for ameliorating adverse effects of focal tunical fibrosis in a subject in need thereof, implemented in a device comprising a wand having a plurality of needles adapted to penetrate a surface of a user's skin, a radio frequency (RF) generator, arranged to deliver RF energy to an area beneath the penetrated skin via at least one needle of the plurality of needles, and a central processing module (CPM), in communication with the wand, and the RF generator operable to control: the depth of penetration of each needle of the plurality of needles, the polarity of each needle of the plurality of needles penetrated into the area beneath the penetrated skin, and an RF energy delivery by the RF generator to the area beneath the penetrated skin, the method comprising: penetrating a skin surface adjacent the focal tunical fibrosis with the plurality of needles; delivering radiofrequency (RF) energy via at least one needle to an area beneath the penetrated skin; controlling, via the central processing module (CPM): penetration depth of each needle; polarity assignment of each needle; and RF energy delivery parameters to the area beneath the skin.

BRIEF DESCRIPTION OF THE DRAWINGS

The features of the devices and methods for ameliorating adverse side effects associated with a sub-cutaneous region exhibiting impedance that is different than the surrounding tissue and/or organ in a subject in need thereof, will become apparent from the following detailed description when read in conjunction with the drawings, which are exemplary, not limiting, wherein like elements are numbered alike in several figures, cross sections are referred to on normal orthogonal coordinate apparatus having XYZ axis, such that Y axis refers to front-to-back, X axis refers to side-to-side, and Z axis refers to up-and-down. and in which.

Figure 1A:
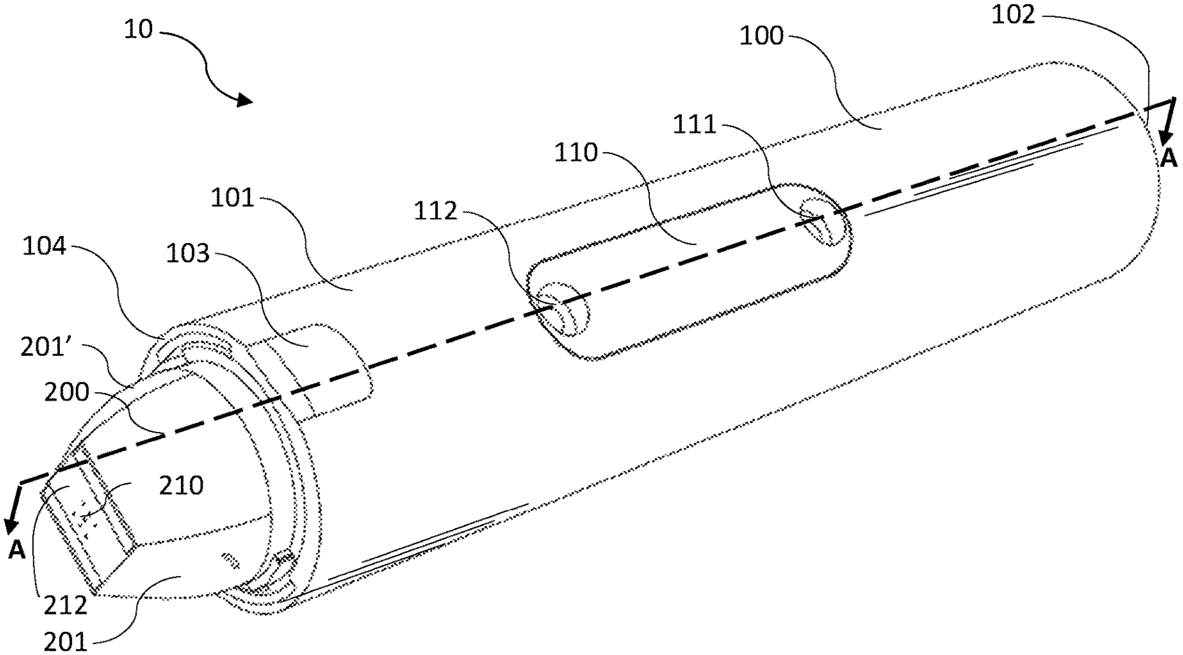
FIG. 1A illustrates a front top perspective view of an exemplary implementation of a wand utilized with the system used to implement some of the methods disclosed, with FIG. 1B illustrating the wand of FIG. 1A at a different angle.

While the disclosure is amenable to various modifications and alternative forms, specifics thereof have been shown by way of example in the figures and will be further described in detail hereinbelow. It should be understood, however, that the intention is not to limit the disclosure to the particular exemplary implementations described. On the contrary, the intention is to cover all modifications, equivalents, and alternatives.

DETAILED DESCRIPTION

The disclosure is directed in one exemplary implementation to devices and methods for ameliorating adverse side effects associated with a sub-cutaneous region exhibiting impedance that is different than the surrounding tissue and/or organ. More specifically, the disclosure is directed to the use of needles equipped with electric impedance sensing and energy discharge capabilities for diagnosing the presence of, and disrupting sub-cutaneous region exhibiting impedance that is different than the surrounding tissue and/or organ, such as, for example focal tunical fibrosis (or plaque), lipomas, and abscesses.

Definitions

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

In the context of the disclosure, the term: "focal tunical fibrosis" refers to localized areas of fibrous tissue formation within the tunica albuginea, the fibrous envelope of the corpora cavernosa in the penis. In certain implementations, the term focal tunical fibrosis is interchangeable with the term "plaque" or "tunical plaque" and their derivative.

In the context of the disclosure, the term "module" refers generally to a logical sequence or association of steps, processes or components. For example, a software module may comprise a set of associated routines or subroutines within a computer program. Alternatively, a module may comprise a substantially self-contained hardware device. A module may also comprise a logical set of processes irrespective of any software or hardware implementation.

A module that performs a function also may be referred to as being configured to perform the function, e.g., a data module that receives data also may be described as being configured to receive data. Configuration to perform a function may include, for example: providing and executing computer code that performs the function; providing provisionable configuration parameters that control, limit, enable or disable capabilities of the module (e.g., setting a flag, setting permissions, setting threshold levels used at decision points, etc.); providing a physical connection, such as a jumper to select an option, or to enable/disable an option; attaching a physical communication link; enabling a wireless communication link; providing electrical circuitry that is designed to perform the function without use of a processor, such as by use of discrete components and/or non-CPU integrated circuits; energizing a circuit that performs the function (e.g., providing power to a transceiver circuit in order to receive data); and so forth.

In the context of the disclosure, the term "operable" means the system and/or the device and/or the program, or a certain element or step is fully functional, sized, adapted and calibrated, comprises elements for, and meets applicable operability requirements to perform a recited function when activated, coupled, implemented, actuated, effected, realized, or when an executable program is executed by at least one processor associated with the system and/or the device. In relation to systems and circuits, the term "operable" means the system and/or the circuit is fully functional and calibrated, comprises logic for, having the hardware and firmware necessary, as well as the circuitry for, and meets applicable operability requirements to perform a recited function when executed by at least one processor.

In an exemplary implementation, the term "electronic communication" refers to a relationship between components that supports electron flow between the components. This may include a direct connection between components or may include intermediate components. Components in electronic communication may be actively exchanging electrons or signals (e.g., in an energized circuit) or may not be actively exchanging electrons or signals (e.g., in a de-energized circuit) but may be configured and operable to exchange electrons or signals upon a circuit being energized. By way of example, two components physically connected via a switch (e.g., a transistor) are in electronic communication regardless of the state of the switch (i.e., open or closed).

The terms "first," "second," and the like, herein do not denote any order, quantity, or importance, but rather are used to denote one element from another. The terms "a", "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the tumor(s) includes one or more tumor). Reference throughout the specification to "one exemplary implementation", "another exemplary implementation", "an exemplary implementation", and so forth, means that a particular element (e.g., feature, structure, and/or characteristic) described in connection with the exemplary implementation is included in at least one exemplary implementation described herein, and may or may not be present in other exemplary implementations. In addition, it is to be understood that the described elements may be combined in any suitable manner in the various exemplary implementations.

As used herein, the term "user interface" refers to, without limitation, any visual, graphical, tactile, audible, sensory, or other means of providing information to and/or receiving information from a user or other entity.

As used herein, the term "memory" or "storage" includes any type of integrated circuit or other storage device adapted for storing digital data including, without limitation, ROM, PROM, EEPROM, DRAM, SDRAM, DDR/2 SDRAM, EDO/FPMS, RLDRAM, SRAM, "flash" memory (e.g., NAND/NOR), and PSRAM.

As used herein, the term "display" means any type of device adapted to display information, including without limitation CRTs, LCDs, TFTs, plasma displays, LEDs (e.g., OLEDs), and fluorescent devices.

As used herein, the term "digital processor" is meant generally to include all types of digital processing devices including, without limitation, digital signal processors (DSPs), reduced instruction set computers (RISC), general-purpose (CISC) processors, microprocessors, field programmable gate arrays (e.g., FPGAs), PLDs, reconfigurable compute fabrics (RCFs), array processors, and application-specific integrated circuits (ASICs). Such digital processors may be contained on a single unitary IC die, or distributed across multiple components, e.g., across PCBs 230, coupled to baseplate 260, and 280 as well as coupled to CPM 800.

Accordingly and in an exemplary implementation, provided herein is a system for use in a procedure for ameliorating adverse side effects associated with a sub-cutaneous region exhibiting impedance that is higher than the surrounding tissue and/or organ in a subject in need thereof, by applying RF energy thereto, the device comprising: a wand having a at least one needle adapted, sized and configured to penetrate a surface of a skin region of the subject; a radio frequency (RF) generator, arranged to deliver RF energy to the sub-cutaneous region exhibiting impedance that is higher than the surrounding tissue and/or organ via the at least one needle; and a central processing module (CPM), in communication with the wand, and the RF generator operable to control: depth of penetration of the at least one needle; intensity of an RF energy delivery by the RF generator to the sub-cutaneous region exhibiting impedance that is higher than the surrounding tissue and/or organ; and optionally, polarity of the at least one needle penetrated into the area beneath the penetrated skin.

In another exemplary implementation, the systems disclosed comprise a device, or several devices for use in a procedure for ameliorating adverse side effects of a focal tunical fibrosis in a patient in need thereof, by applying RF energy thereto, the device comprising: a wand having a plurality of needles adapted to penetrate a surface of a user's penile skin; a radio frequency (RF) generator, arranged to deliver RF energy to an area beneath the penetrated penile skin via at least one needle of the plurality of needles; and a central processing module (CPM), in communication with the wand, and the RF generator operable to control: the depth of penetration of each needle of the plurality of needles; the polarity of each needle of the plurality of needles penetrated into the area beneath the penetrated skin; and an RF energy delivery by the RF generator to the area beneath the penetrated skin. In other words, the devices disclosed comprises a wand with multiple needles (typically 16-34 gauge, e.g., medical-grade stainless steel) designed to penetrate penile skin superficially while avoiding deeper vascular structures. The RF generator (operating at 300 kHz-64 MHz) is operable to delivers controlled energy through selected needles, with power output adjustable between for example about 1 Watt and about 30 W based on impedance feedback. The central processing module (CPM) regulates penetration depth via motorized actuators having resolution of ±0.1 mm and dynamically assigns needle RF phase to optimize current paths through fibrotic tissue. This tripartite system enables precise spatial control of RF-induced thermal effects (targeting temperatures between about 36° C.-and about 93° C.), while minimizing collateral damage. In certain exemplary implementations, the penetration depth is between about 0.5 mm, and about 15 mm, from the surface into the tunical fibrosis.

The systems described herein may be configured to generate RF energy and to apply the generated RF energy to a penis to thereby elevate a temperature of the focal tunical fibrosis above a predetermined temperature value while maintaining the penile surface below a predetermined temperature threshold, for example, below 42° C. The predetermined temperature value and profile may be configured to initiate remodeling and/or a regeneration of collagen fibers, smooth muscle cells and elastin fibers in the specific plaque area.

As indicated, generating RF energy for heating involves the use of radio frequency (RF) electromagnetic waves, for example, in the range of 300 kHz to 63 MHz. The RF generator functions in an exemplary implementation, by creating an oscillating electric current, which passes through at least one of the needles in penetrating the tissue. This current induces in turn, the oscillation of ions within the immediate area, generating heat through resistive or dielectric heating mechanisms to produce thermal effects in, for example the focal tunical fibrosis by translating kinetic energy of polar molecules, such as water and certain other molecules, to thermal energy.

The control of an RF generator can be achieved through the central processing module (CPM), which regulates parameters such as frequency, power output, needle polarity or RF phase and duration of the RF energy application (in other words, the predetermined action protocol). This precise control allows for targeted heating, minimizing damage to surrounding tissues, as well as maintaining the penis surface temperature below the desired threshold, while maximizing therapeutic effects. The CPM can be programmed with predetermined operation patterns, ensuring consistent and effective delivery of RF energy tailored to the specific requirements of the treatment area commensurate with the severity of the condition.

Additionally, the CPM further comprises at least one processor in communication with a non-transitory memory device, storing thereon a computer-readable media with a set of executable instructions configured, when executed by the at least one processor to: selectably control penetration depth of each needle of the plurality of needles; detect electrical impedance measured in each needle of the plurality of needles penetrated to the area beneath the penetrated skin; and dynamically assign RF phase or polarity to each needle of the plurality of needles penetrated to the area beneath the penetrated skin, based on the detected impedance. The CPM's processor e.g., ARM Cortex-M7, can be configured to execute impedance measurement algorithms with sampling rate of, for example 1 kHz, detecting tissue resistance between about 50 ohm (Ω) and about 600Ω, differentiating fibrotic plaques from healthy tunica albuginea tissue. Also, penetration depth control can be implemented using, for example, servo motors or step motors with, e.g., optical encoders (having ±0.05 mm accuracy), while polarity assignment can follow combinatorial optimization routines configured to maximize current density through high-impedance regions. In certain circumstances, the dynamic impedance mapping can be configured to update every 50 ms., thereby enabling real-time adjustment of RF parameters via the equation P=V2/RP=V2/R, where delivered power (P) is modulated to maintain tissue temperatures at a predetermined value.

In certain exemplary implementations, the devices provided, used to implement the methods disclosed, further comprising at least one electrode positioned (i) on the wand between adjacent needles, (ii) on a deployable substrate adjacent to the penile skin, (iii) as conductive segments on a subset of needles, or a plurality of electrodes disposed on at least two of the forgoing locations, wherein the CPM is configured to: dynamically assign anode and cathode roles to individual needles and electrodes to establish rotating multipolar RF circuits; compute a tissue impedance gradient map from measurements across all active needles and electrodes; and selectively modulate RF energy distribution to maintain a predetermined impedance variance and a predetermined thermal gradient.

In certain exemplary implementations, the devices provided, used to implement the methods disclosed, further comprising at least one electrode positioned (i) on the wand between adjacent needles, (ii) on a deployable substrate adjacent to the penile skin, (iii) as conductive segments on a subset of needles, or a plurality of electrodes disposed on at least two of the forgoing locations, wherein the CPM is configured to: dynamically assign anode and cathode roles to individual needles and electrodes to establish rotating multipolar RF circuits; compute a tissue impedance gradient map from measurements across all active needles and electrodes; and selectively modulate RF energy distribution to maintain a predetermined impedance variance and a predetermined thermal gradient.

The electrode's positioning can be optimized to align with clinical objectives. For example, in superficial plaques, a surface electrode placed externally on the penile skin could serve as a return path, allowing the CPM to modulate energy delivery based on real-time impedance measurements between the needle and the electrode. For deeper or irregularly shaped plaques, a second needle-style electrode integrated into the wand could be inserted parallel to the primary needle, creating a controlled bipolar circuit within the tunical layer, enabling the CPM to dynamically adjust the inter-electrode distance and polarity, tailoring the RF field's geometry to match the lesion's dimensions. Additionally, or alternatively, a ring electrode circumferentially mounted on the wand's shaft could be used to provide continuous feedback on superficial tissue temperature or impedance, acting as a safeguard against unintended epidermal heating.

The electrode(s) also introduce advanced sensing capabilities that can be used together with the CPM's control algorithms. By measuring electrical impedance between the needle and electrode, the system can detect real-time changes in tissue composition, such as collagen denaturation during RF application, and automatically terminate energy delivery once a predefined impedance threshold resulting from collagen denaturation is achieved, ensuring consistent therapeutic outcomes. Temperature sensors embedded in the electrode could further enhance safety by triggering energy modulation if localized heating exceeds safe limits. These feedback mechanisms transform in certain exemplary implementation, the device from an open-loop system reliant on operator judgment to a closed-loop platform that self-optimizes treatment parameters based on direct tissue response In yet other exemplary implementations, incorporating electrodes into the device when implemented using a multipolar RF needle array can further amplify the system's capacity to achieve homogeneous collagen remodeling across complex fibrotic geometries, while maintaining sub-millimeter control over thermal gradients. To reiterate, in a multipolar configuration, RF current flows between multiple active needles rather than a single needle-electrode pair, creating overlapping electromagnetic fields that can collectively denature collagen. However, using the electrode(s) disclosed as part of the device, address uneven energy distribution due to variable tissue impedance between needles and insufficient real-time feedback. Introducing electrodes, whether standalone components, or integrated into the needle array, can transform the ablation dynamics by enabling dynamic circuit reconfiguration, impedance-based lesion mapping, and closed-loop thermal regulation.

Accordingly, and in another exemplary implementation positioning electrodes within the needle array can be used to optimize energy delivery. For example, embedding microelectrodes on the non-insulated shafts of alternating needles allows the CPM to toggle between monopolar, bipolar, and multipolar modes based on plaque morphology. Surface electrodes placed on the penile shaft can be used to add another layer of control by serving as external reference points for impedance tomography, allowing the system to model current dispersion in three dimensions and adjust needle activation sequences to prevent undertreatment of deep tunical layers. Likewise, integrating electrodes further enables multispectral sensing capabilities useful in adaptive therapy. By measuring impedance differentials between needle-electrode pairs, the CPM can be configured to construct a real-time conductivity map that identifies regions of residual fibrosis (high impedance due to dense collagen cross-linking) versus adequately treated tissue (lower impedance post-denaturation).

Temperature sensors co-located with electrodes can further enable gradient-based thermal profiling. For example, if one quadrant or other sub-region of the array detects temperatures exceeding 47° C. (a typical threshold for collagen shrinkage), the CPM can be configured to redistribute RF current to cooler zones via alternative electrode/needle pathways. This dual feedback mechanism can be used to ensure the ablation zone remains within the therapeutic window (e.g., between about 40° C., and about 63° C.) for controlled collagen remodeling without inducing necrotic hotspots. Furthermore, phase-sensitive voltage measurements between electrodes can be used to detect microbubble formation, which is a common cause of impedance spikes for triggering automatic energy titration to maintain consistent tissue coupling.

Typical average size of focal tunical fibrosis varies, but typically ranges between about 0.5 cm. and about 3.5 cm in length, between about 0.5 cm. and about 2.0 cm in width, and between about 0.2 cm and about 1.0 cm in thickness. The plaques are usually oval or irregular in shape, with varying thicknesses that can contribute to the overall severity of the condition. In the devices disclosed, the CPM is operable to cause at least one needle, for example, the needle where the sensed impedance indicates the tunical plaque, of the plurality of needles, to penetrate between 1 mm and 3 mm into the focal tunical fibrosis. In other words, the needle penetration is constrained to 0.1 mm-10 mm, more precisely, between about 0.1 mm and about 10 mm. through mechanical stops and CPM limits encoded in the set of executable instructions, targeting the tunica albuginea's average thickness. Depth calibration can be achieved using e.g., optical microsensors at needle bases, optionally verified against ultrasound imaging during preclinical testing. This range is configured to prevent urethral/perforator vessel injury while ensuring sufficient energy deposition into the fibrous matrix.

When the wand is positioned on the penis, at least one of the plurality of needles are configured to penetrate the focal tunical fibrosis (intraplaque), at an approach angle α, of between about 0° and 90° off horizontal, initially disrupting the intraplaque mechanically, followed when selected, remodeling intraplaque by elevating the temperature of the focal tunical fibrosis to a temperature of between 36° C. and 93° C. (e.g., for ablation, when required), while maintaining the penis surface immediately under the platform below threshold temperature, for example 42° C. Accordingly, each needle of the plurality of needles can be sized and configured to penetrate the surface of the user's skin adjacent the focal tunical fibrosis at an approach angle of between 0° and 90° off horizontal. The insertion approach angle e.g., 15°-75° in certain exemplary implementation, can be affected through either articulating needle guides in the wand, or, as depicted in FIG. 1, through selection and rotation of the rings, allowing tangential access to plaque margins. In certain exemplary implementation calculation of the approach angle can depend on the plaque properties, for example θ=arctan (h/d), where h=plaque thickness (e.g., between about 0.5 mm and about 3.0 mm) and d=lateral spread (e.g., between about 3 mm, and about 8 mm). For example, angles of over about 60° can be used to facilitate mechanical focal fibrosis disruption, while shallow angles of, for example, less than about 30°, can be used to enable broad-area modulation.

The needles can be formed from metals such as stainless-steel (e.g., 316L), gold, and titanium and be further configured to limited current conduction on specific part of the needle using insulation. Palladium, nickel, palladium-cobalt alloys and Tungsten can also be used. The needle array in the wand, can have for example, between 1 and 128 needles, or between 4 needles and 36 needles, and be configured to variably and selectably (in other words, without affecting other operational parameters), extend from the surface of the wand between about 1 mm and 12 mm, for example, between 1.5 mm and 9 mm, or between about 1 mm and about 3 mm into the plaque. Accordingly, when the penis is positioned in the wand, the needles are configured to penetrate the focal tunical fibrosis (thus intraplaque), elevating the temperature of the focal tunical fibrosis to a temperature of between 36° C. and 93° C., while maintaining the penis surface immediately under the wand below threshold temperature, for example 42° C. Furthermore, the selected needle configuration is configured to balance treatment density, for example 2-8 needles/cm$^2$, with procedural practicality. For circumferential plaques, concentric arrays (12-24 needles), when coupled with the proper polarity selection, create overlapping ablation zones, while small focal lesions use different clusters ensuring sufficient separation to prevent thermal overlap.

In another exemplary implementation, as illustrated in FIG. 1, the plurality of needles are arranged in a plurality of concentric rings, each ring comprising at least a pair of diametrically opposed needles. Additionally, each ring can be configured to be rotatably coupled to the wand while CPM can be configured to control which of the plurality of needles in each ring will extend, and what polarity will be assigned, thereby determining approach angle and field density and shape. For example, rotatable needle rings (3-6 rings/wand see e.g., FIG. 1) enable circumferential treatment patterns. Each ring contains 4-8 diametrically opposed needles (e.g., 316L stainless steel) mounted on motorized carriages (rings). Rotation (0-360°±1° precision) coordinates with CPM-controlled extension/retraction sequences, allowing spiral ablation patterns. When needles are deployed in a radial pattern around a central fibrotic cord, the CPM can activate peripheral needles as anodes and the central needle as a cathode, creating a converging RF field that concentrates energy at the plaque's core. Conversely, for diffuse fibroses, the CPM might designate adjacent needles as alternating anodes and cathodes, generating interstitial current paths that homogenize heating.

Furthermore, each needle of the plurality of needles can be further adapted, sized and configured to physically disrupt the focal tunical fibrosis. For example and in yet another implementation, needle tips are designed to feature microserrations (20-50 μm teeth) and asymmetric bevels to mechanically disrupt collagen crosslinks. Optional axial vibration (50-200 Hz) during insertion can further amplify plaque microfracture disrupting fibrous septa without complete transection. Conversely, post-disruption RF delivery (e.g., 1-15 W) then enhances collagen remodeling through controlled denaturation.

In certain implementations, insulation of, for example, multilayer polyimide/Teflon or Parilene coatings (50-150 μm thick) covering 70-90% of needle length, and leaving 1-3 mm active tips can be used to focus and confine current density (J=I/A), where A=uninsulated surface area) to, for example, 0.5-2 A/mm$^2$, preventing superficial epidermal heating. Accordingly, a first needle portion of the plurality of needles used in the devices provided, and used to implement the methods disclosed, can be insulated, and a second needle portion of the plurality of needles is uninsulated.

As was noted; Peyronie's disease (PD) can typically be classified by several stages; the first is an acute stage characterized by progression of penile deformity and may be associated with local pain in the erect and/or flaccid states. The length of the acute phase varies typically from 6-18 months. Conversely, the chronic phase is characterized by stability of penile deformity for at least 3-6 months, with amelioration or total elimination of the local pain.

In other words, and in an exemplary implementation, the number and polarity configuration used in the methods disclosed, implemented using the devices described, is disease stage dependent as determined from impedance measurements performed using the device.

To reiterate, Peyronie's disease (PD) is characterized by focal fibrotic plaques within the tunica albuginea, leading to penile deformity and functional impairment. While current treatment modalities address the molecular, histological, and biomechanical aspects of these plaques, their electrical properties, such as impedance differences relative to surrounding tissues, is not currently addressed.

Not wishing to be bound by theory, it is apparent that fibrotic plaques in PD are marked by excessive deposition of disorganized collagen types I and III, reduced elastin fiber density, and potential calcification over time. Collagen-rich tissues typically exhibit altered dielectric properties due to their dense extracellular matrix (ECM) structure. The increased collagen content and cross-linking in PD plaques would ostensibly reduce water mobility within the ECM, which would be likely to elevate electrical impedance compared to a normal (non-PD) tunica albuginea. Calcified plaques, a late-stage feature of PD, would further amplify impedance differences, as mineralized deposits are poor conductors of electrical current.

Furthermore, the cellular microenvironment of PD plaques can contribute to potential impedance variations. Myofibroblasts, which dominate fibrotic lesions, exhibit distinct membrane properties and enhanced contractile activity driven by TGF-β1 signaling. These cells may alter local ion channel expression or extracellular ion distribution, indirectly influencing tissue conductivity. Additionally, imbalances in matrix metalloproteinases (MMPs) and tissue inhibitors of metalloproteinases (TIMPs) typically associated with certain stages of PD plaques could modify the ECM's porosity and hydration, further modulating electrical behavior.

Considering the need to elevate temperature enough up to and including to achieve ablation temperature, or severe coagulation temperature, it is contemplated to deliver RF at a frequency of between about 300 kHZ and about 63 MHZ.

Accordingly and in certain exemplary implementations, the devices described herein, used to implement the methods provided, further comprise a user interface (see e.g., FIG. 5A, 5B), wherein the set of executable instructions is further configured, when executed by the one processor to cause the CPM to: identify a needle of the plurality of needles determined to have impedance associated with the focal tunical fibrosis; classify the focal tunical fibrosis based on the measured impedance; using the user interface, indicate a focal tunical fibrosis class; based on the classification, determine an action regimen comprising: determining the number of needles configured to penetrate the area beneath the penetrated skin adjacent the needle of the plurality of needles determined to have impedance associated with the focal tunical fibrosis; determine the depth of penetration of each needle of the plurality of needles configured to penetrate the area beneath the penetrated skin adjacent the needle of the plurality of needles determined to have impedance associated with the focal tunical fibrosis; assign the polarity of each needle of the plurality of needles configured to penetrate the area beneath the penetrated skin adjacent the needle of the plurality of needles determined to have impedance associated with the focal tunical fibrosis; determine an RF intensity delivered to each needle of the plurality of needles configured to penetrate the area beneath the penetrated skin adjacent the needle of the plurality of needles determined to have impedance associated with the focal tunical fibrosis; and execute the action regimen.

For example, the GUI utilizes a classification matrix where impedance (Z) and its rate of change (dZ/dt) during RF delivery is used to categorize plaques and design an action protocol:

Class I (Z<100Ω, dZ/dt>−5 Ω/s): Early fibrosis→45° C., 30 s

Class II (100-200Ω, dZ/dt −5-−10 Ω/s): Mature plaque→55° C., 60 s

Class III (Z>200Ω, dZ/dt<−10 Ω/s): Calcified→mechanical disruption+60° C., 90 s Action regimens auto-populate based on classification, with override capability via touchscreen. Post-treatment reports document parameter matrices and thermal dose (CEM43>120 min)

Additionally, the polarity of the selected needle of the plurality of needles determined to have impedance associated with the focal tunical fibrosis (e.g., is higher) is different than the polarity of the plurality of needles determined not to have impedance associated with the focal tunical fibrosis (in other words, having lower impedance). For example, polarity inversion protocols are used in certain exemplary implementations, to assign alternating +/−voltages (50-200 Vpp) to adjacent needles, creating focused electric field gradients where ∇V=20-50V/mm, for example through high-impedance zones. IN the protocol, the CPM can implement a dynamic dipole algorithm where:

If $Z_n > Z_{avg} + N\sigma \rightarrow$ anode (+)

Else→cathode (−)

Where Zn is the impedance in ohm measured in needle n, $Z_{avg}$ is the average impedance measured across all needles selected to penetrate the tissue, N is an integer between 1-3 (user defined or assessed through machine learning), and σ is the standard deviation of the impedance readings.

Using the assignment algorithm can increase current density in fibrotic regions by 3-5× compared to uniform polarity, enhancing thermal penetration while sparing normal tunica.

In an exemplary implementation, the devices disclosed are used to implement the methods provided. The method involves penetrating the penile skin adjacent to focal tunical fibrosis using a wand equipped with multiple needles, followed by controlled RF energy delivery to the subdermal target area. The CPM regulates at least three parameters: needle penetration depth through motorized actuators with ±0.1 mm precision, polarity assignment via solid-state relays switching at 1 kHz, and RF power modulation (1-30 W) based, for example, on real-time tissue feedback. Penetration can occur in staged sequences—initial insertion to 0.5 mm, impedance measurement, then final depth adjustment—to ensure optimal energy coupling. RF delivery follows temperature-controlled protocols maintaining for example, 36°-83° C. for between about 30 seconds and about 90 seconds, with thermal sensors optionally embedded in needle tips validating intraprocedural conditions.

In yet another exemplary implementation, the systems and methods disclosed, are used to ameliorate side effects associated with other phenomena expressed as sub-cutaneous regions exhibiting (electric) impedance that is different than the surrounding tissue and or organ. These sub-cutaneous regions can be, for example, Lipomas, fibroids, and abscesses. For example, the sub-cutaneous region exhibiting impedance that is different than the surrounding tissue and/or organ, is a lipoma, or an abscess, each exhibiting a lower impedance than the surrounding tissue and/or organ.

For example, in the case of lipoma, the systems and methods disclosed can be used as a treatment co-modality, with liposuction, where pretreatment using these systems and methods can confer several benefits. For example, the focused, RF-mediated thermal effect can soften and emulsify the lipoma, thus making aspiration by liposuction less traumatic and possibly more effective, especially in cases of large, fibrous, or multilobulated lipomas that are otherwise difficult to extract due to their consistency or adherence to surrounding structures. Additionally, using the methods and systems disclosed can provide a hemostatic benefit; by coagulating small blood vessels within and around the lipoma, thereby reducing intraoperative bleeding and post-operative hematoma formation (and consequently, healing).

Other treatment co-modalities, can be for example, in cases where complete excision of the lipoma is desirable but anatomical and/or physiological constraints exist, where the systems and methods disclosed can be used, alongside tumescent anesthesia (referring to injection of dilute anesthetic solution, often with epinephrine and sodium bicarbonate, into the tissue until it becomes firm and swollen, which itself facilitates liposuction by hydro-dissecting tissue, reducing bleeding, and providing local analgesia), to further lower procedural trauma.

In certain other exemplary implementations, for example in treating adverse side effects associated with abscesses, delivering RF energy into the abscess core via a needle array can be configured to induce localized heating, thereby sterilizing the infected contents, ablating bacteria, and collapsing the abscess cavity via coagulation of proteins and destruction of the wall. Furthermore, as a pretreatment before I&D or needle aspiration, using the systems and methods disclosed, can be configured to partially liquefy thick pus or necrotic debris, making evacuation easier in cases where abscesses are loculated, viscous, or poorly drained by standard means. Furthermore, the systems and methods disclosed can be potentially used to identify loculated abscesses, by identifying impedance differentials. This can be accentuated since pus in abscesses is an ionic conductor that is different than healthy surrounding tissue.

In certain exemplary implementations, the systems disclosed are used to implement the methods provided. Accordingly and in another exemplary implementation, provided herein is a method for ameliorating adverse side effects associated with a sub-cutaneous region exhibiting impedance that is different than the surrounding tissue and/or organ, in a subject in need thereof, implemented in a device comprising a wand having a plurality of needles adapted to penetrate a surface of a user's skin, a radio frequency (RF) generator, arranged to deliver RF energy to an area beneath the penetrated skin via at least one needle of the plurality of needles, and a central processing module (CPM), in communication with the wand, and the RF generator operable to control: the depth of penetration of each needle of the plurality of needles, an intensity of RF energy delivery by the RF generator to the area beneath the penetrated skin, and optionally, the polarity of each needle of the plurality of needles penetrated into the area beneath the penetrated skin, the method comprising: penetrating a skin surface above sub-cutaneous region with the plurality of needles; delivering radiofrequency (RF) energy via at least one needle to the sub-cutaneous region; controlling, via the central processing module (CPM): penetration depth of each needle; RF energy delivery parameters to the area beneath the penile skin; and Optionally, polarity assignment of each needle.

Furthermore and in yet another exemplary implementation, provided herein is a method for ameliorating adverse effects of focal tunical fibrosis in a subject in need thereof, implemented in a device comprising a wand having a plurality of needles adapted to penetrate a surface of a user's skin, a radio frequency (RF) generator, arranged to deliver RF energy to an area beneath the penetrated skin via at least one needle of the plurality of needles, and a central processing module (CPM), in communication with the wand, and the RF generator operable to control: the depth of penetration of each needle of the plurality of needles, the polarity of each needle of the plurality of needles penetrated into the area beneath the penetrated skin, and an RF energy delivery by the RF generator to the area beneath the penetrated skin, the method comprising: penetrating a skin surface adjacent the focal tunical fibrosis with the plurality of needles; delivering radiofrequency (RF) energy via at least one needle to an area beneath the penetrated penile skin; controlling, via the central processing module (CPM): penetration depth of each needle; polarity assignment of each needle; and RF energy delivery parameters to the area beneath the penile skin.

A more complete understanding of the components, methods, and devices disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof, their relative size relationship and/or to define or limit the scope of the exemplary embodiments. Although specific terms are used in the following description for the sake of clarity, these terms are intended to refer only to the particular structure of the embodiments and examples selected for illustration in the drawings, and are not intended to define or limit the scope of the disclosure. In the drawings and the following description below, it is to be understood that like numeric designations across different figures refer to components of like function. As indicated, cross sections are referred to on normal orthogonal coordinate apparatus having XYZ axis, such that Y axis refers to front-to-back, X axis refers to side-to-side, and Z axis refers to up-and-down.

Turning now to FIGS. 1A-5B, illustrating an exemplary implementation of system 20 (see e.g., FIG. 5A, 5B), for use in a procedure for ameliorating adverse side effects of a focal tunical fibrosis (or Pyrone's disease (PD)), in a subject (e.g., a patient) in need thereof, by applying RF energy thereto, the device comprising: wand 10 having a at least one $i^{th}$ needle 210*i* (see e.g., FIG. 3B) adapted, sized and configured to penetrate the surface of the subject's penile skin; radio frequency (RF) generator 850, arranged to deliver RF energy to an area beneath the subject's penetrated penile skin via at least one $i^{th}$ needle 210*i*; and a central processing module (CPM) 800 (see e.g., FIG. 5A), in communication with wand 10, and the RF generator 850 operable to control: depth of penetration of the at least one $i^{th}$ needle 210*i*; polarity of the at least one $i^{th}$ needle 210*i* penetrated into the area beneath the subject's penetrated skin; and intensity of an RF energy delivery by RF generator 850 to the area beneath the penetrated skin.

Figure 1B:
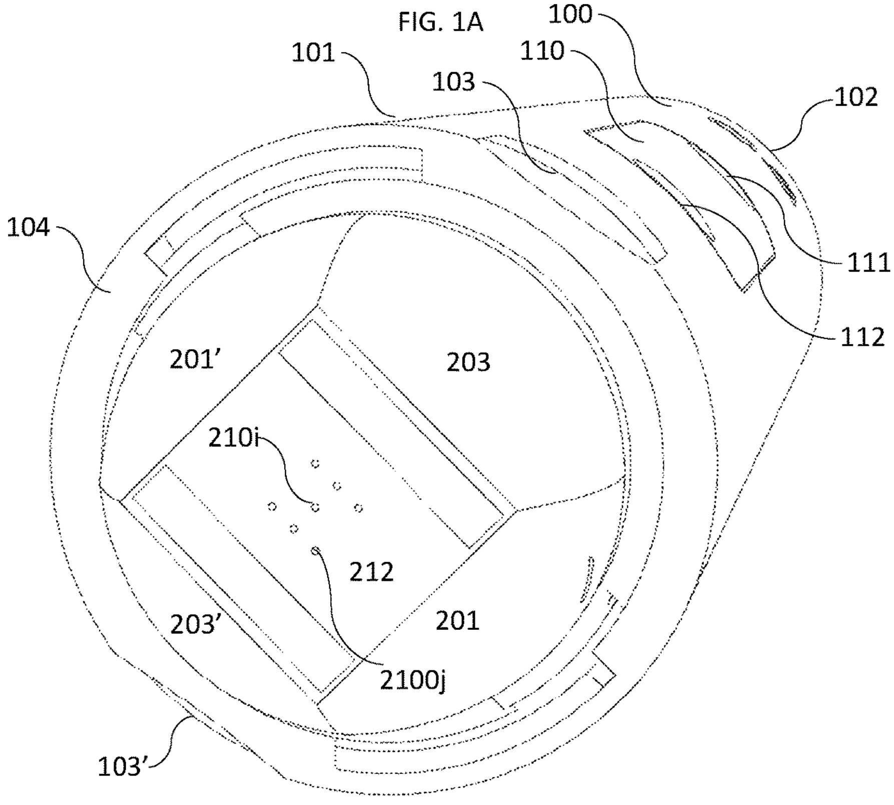
Figure 2:
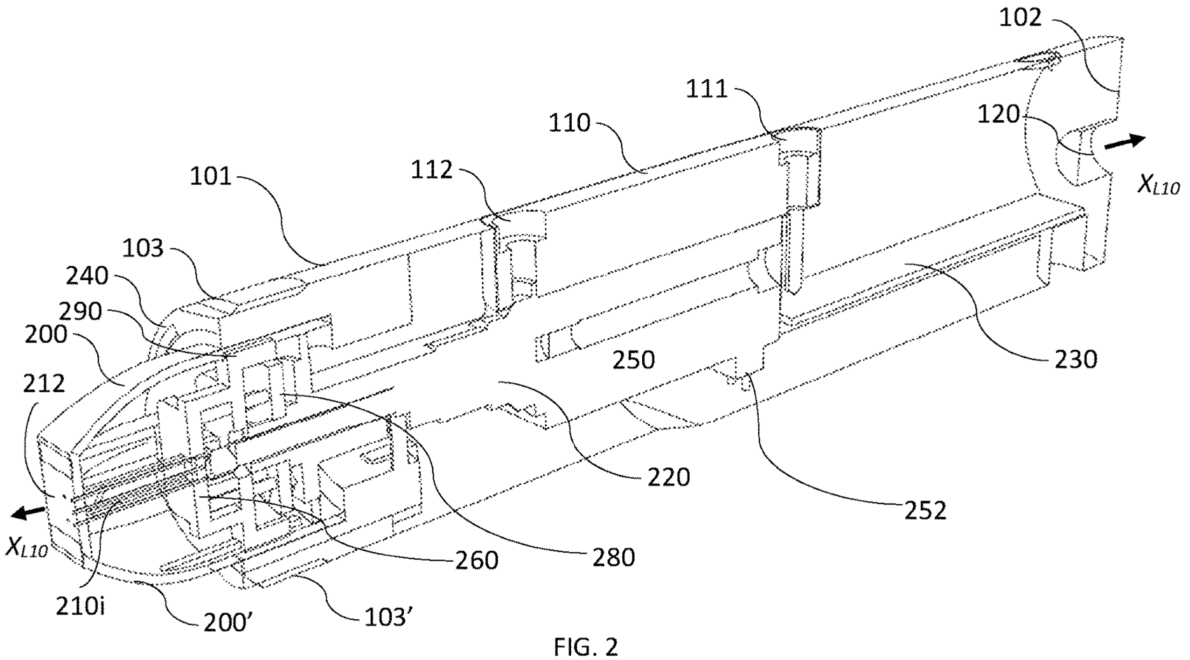
FIG. 2, illustrates X-Z cross section of the wand taken along line A-A in illustrated in FIG. 1A.
Figure 3A:
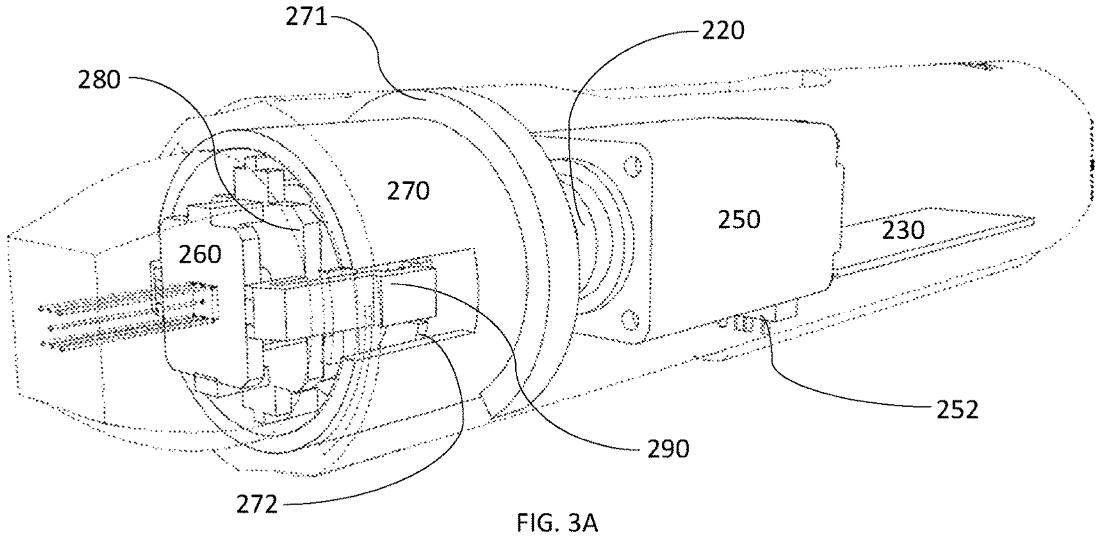
FIG. 3A illustrates an exemplary implementation of the internal components of the wand, with FIG. 3B illustrating the head portion of the wand illustrated in FIG. 1A.

In certain exemplary implementations (see e.g., FIG. 1A-4B), wand 10 defining longitudinal axis $X_{L10}$ (see e.g., FIG. 2), further comprises: shell 100, having proximal end 102 operably coupled to RF generator 850 (see e.g., FIG. 5A, 5B), actuator 250 (see e.g., FIGS. 2, 3A, 4A, 4B)—disposed within shell 100, in communication with CPM 800, actuator 250 operable to selectably advance one $i^{th}$ needle 210*i* or more needles in array of plurality of needles 210*i*, each one $i^{th}$ needle 210*i* to depth determined by CPM 800 (and a user in control of the CPM, namely a physician or operator), head portion 30 (see e.g., FIG. 3B), comprising: plunger 281 coupled to actuator 250, flanged 271 handle ring 270 (see e.g., FIGS. 3A, 4A, 4B), insulating ring 240, needle array carrier 290, needle array base plate 260 (see e.g., FIGS. 2, 3A, 3B) coupled to needle array carrier 290, and cap 200, defining distal end 212, distal end 212 defining plurality of apertures 2100*j* (see e.g., FIG. 1B) adapted, sized and configured to accommodate passage of at least one $i^{th}$ needle 210*i*, cap 200 coupled to needle array carrier 290 (see e.g., FIGS. 2, 3A).

Figures 5A, 5B:
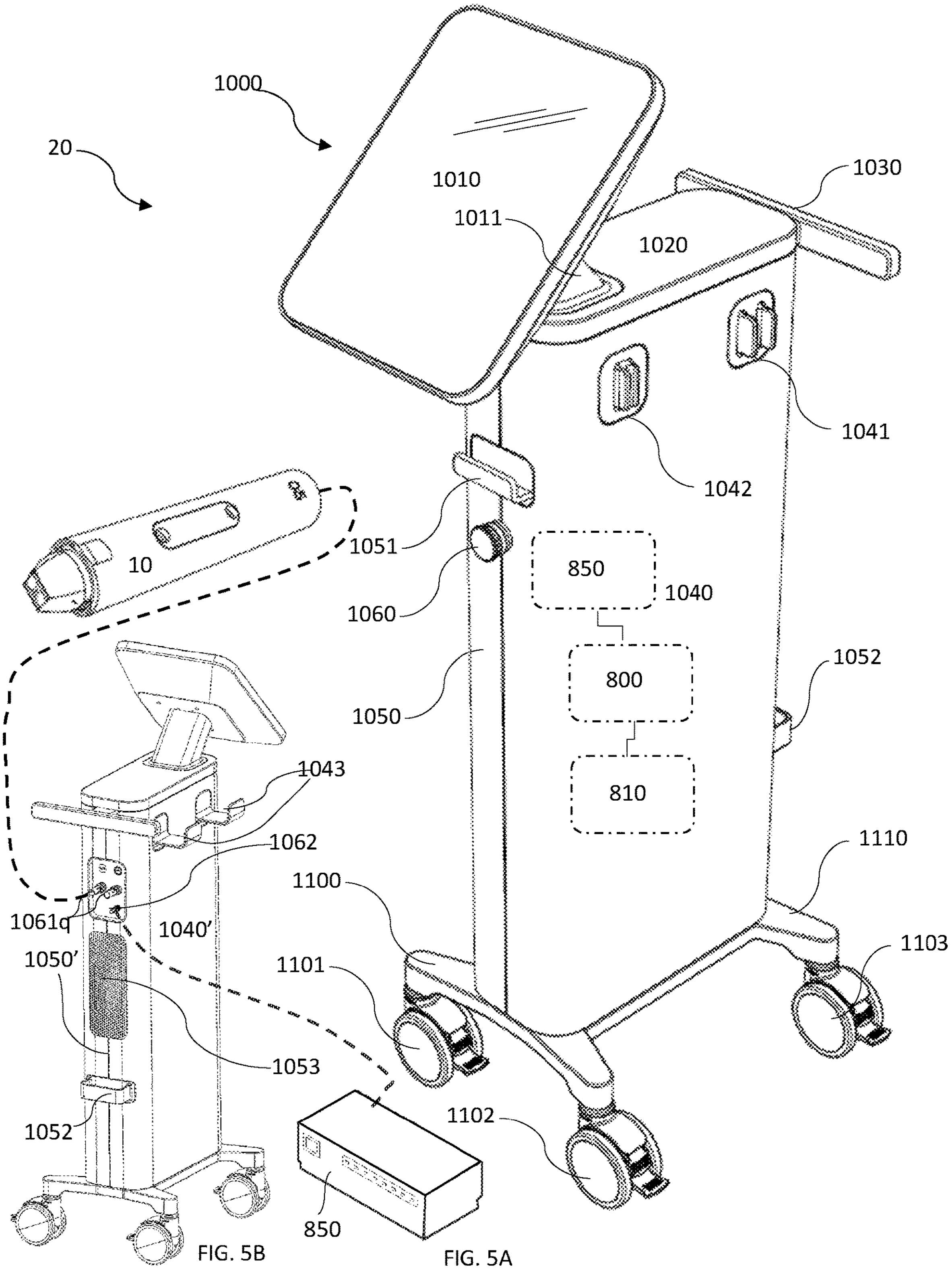
FIG. 5A, illustrates another exemplary implementation of the system, including a cart with FIG. 5B, illustrating a rear view of the cart.

As further illustrated in FIGS. 1A, 1B, and 2, shell 100 comprises proximal end 102 defining aperture 120, configured to accommodate, for example a connector cable 1200 (not shown, see e.g. FIG. 5A). Shell 100 also has body portion 101 with distal end 104, a release tab 103 and control pad 110 with various buttons 111, 112. Cap 200, further defines dorsal facet 201, and ventral facet 201' (see e.g., FIG. 1B) as well as side facets 203, 203'. Furthermore, and as illustrated in FIG. 1B, the needle array apertures 2100*j* can be arranged as shown in an H shape, with seven (7) $j^{th}$ apertures 2100*j* arranged in two rows of three (3) $j^{th}$ apertures 2100*j*, with one $j^{th}$ apertures 2100*j* central between the two rows, all located centrally on distal end 212 of cap 200.

Figure 3B:
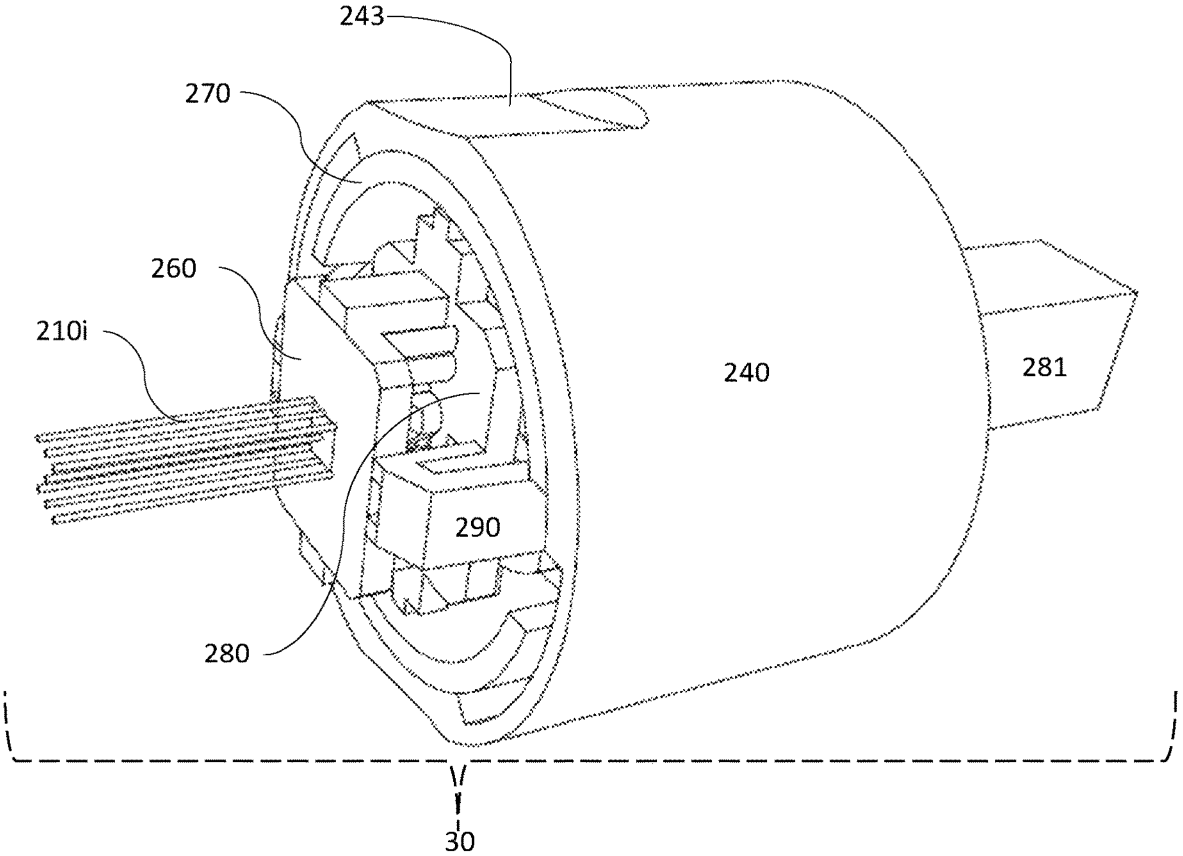
Figure 4A:
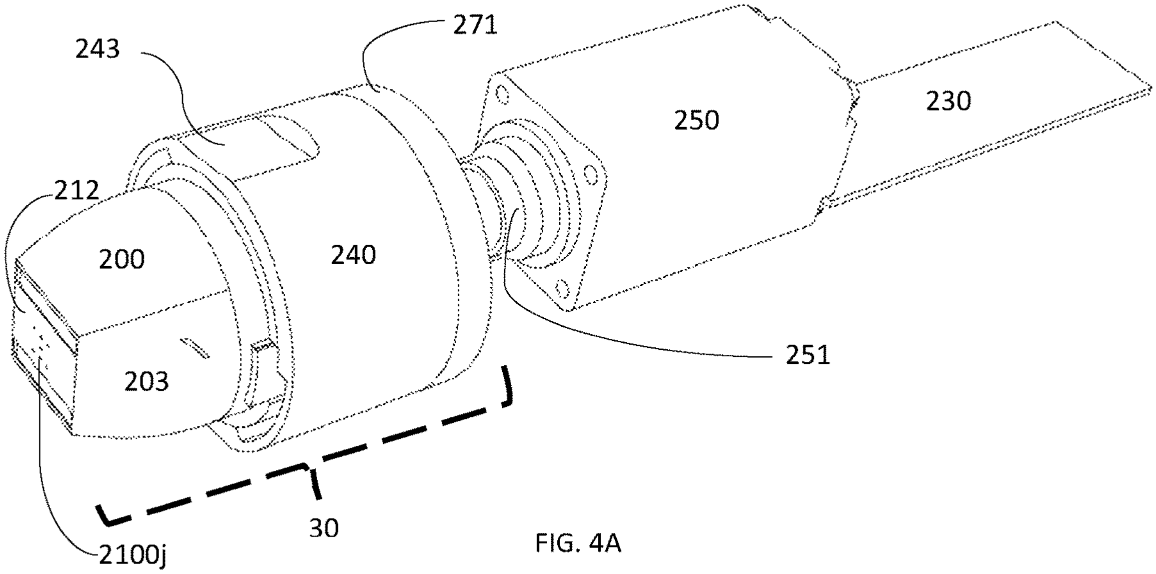
FIG. 4A, illustrates an exemplary implementation of internal components' architecture, with FIG. 4B, illustrating and exploded view thereof.
Figure 4B:
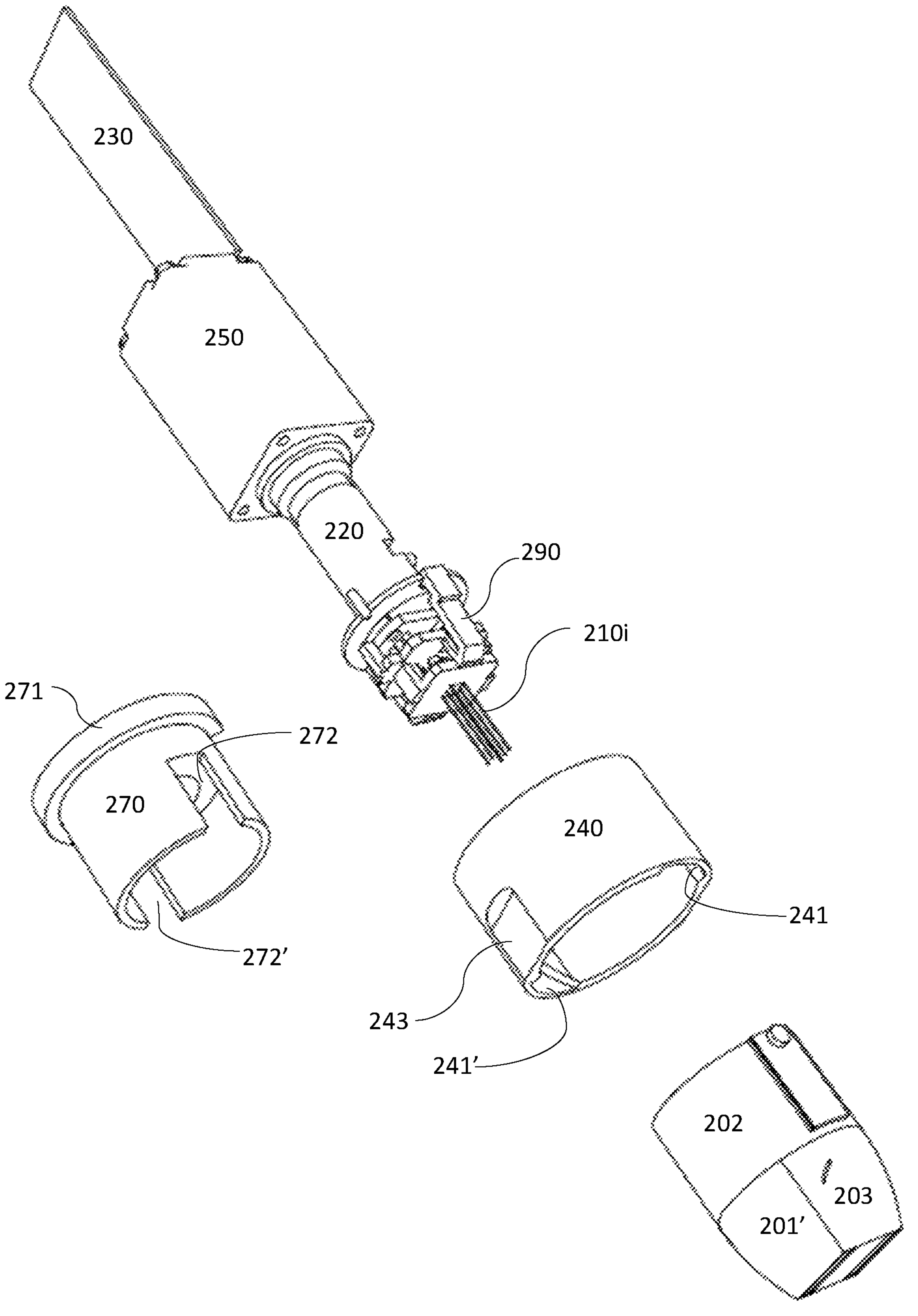

However, the skilled artisan would readily recognize that any needle array arrangement could be used, having, for (a non-limiting) example, plurality of rings, squares, or parallel lines each arrangement comprising at least a pair of diametrically opposed needles, and wherein each ring is rotatably coupled to the wand. Accordingly, and in yet another exemplary implementation, head portion 30, illustrated in FIGS. 3B, and 4A is interchangeable with another head portion (40, not shown), where e.g., base plate 260 is configured to support a different arrangement of needle array 210*i*, while needle array apertures 2100*j* is configured to accommodate each $i^{th}$ needle 210*i*, all located centrally on distal end 212 of cap 200.

In other words, the modular and interchangeable nature of head portion 30 (40, 50 etc.) of wand 10 can enable wide range of clinical applications by allowing the practitioner to select specific needle array 210*i* configuration best suited for the morphology of the subcutaneous region being treated. The system comprises several distinct, and interchangeable head portions 30, 40 etc., each comprising unique arrangement of $i^{th}$ needle 210*i*, supported by needle array 210*i* base plate 290 and accommodated by corresponding pattern of apertures in needle array apertures 2100*j* in cap 200. Head portion 30 modularity enables wand 10 to be readily adapted for treating lesions of varying size, shape, and depth, from broad, diffuse areas of fibrosis to small, discrete nodules. The mechanical and electrical interface between wand 10 main body 100, containing actuator 250, and interchangeable head portion 30, 40, etc., is standardized, ensuring that CPM 800 can precisely control depth, polarity, and RF energy delivery for any attached head portion 30 configuration.

In another exemplary implementation, the needle array 210*i* is be configured as a rectilinear grid arranged in squares, typically comprising 4, 9, or 16 needles positioned at equidistant nodes. Likewise, alternating rows may be configured with insulated and non-insulated segments along the needle shaft, enabling deep focal penetration with limited surface conduction. Such a square matrix allows for uniform coverage of broader, planar regions of abnormal tissue, such as large lipomas or multiloculated abscesses, in which diffuse current distribution may be preferable. The modularity of the square grid configuration can enable selective activation of columns or diagonals, such that the CPM 800 can dynamically focus RF delivery in response to real-time impedance mapping, while still preserving the geometric integrity of array 210*i* grid for energy symmetry.

In yet another exemplary implementation, a head portion 50, supporting a minimal two-needle array 210*i* may be deployed, where the pair of needles are diametrically opposed relative to a central axis of wand 10. This configuration can be beneficial in circumstances such as, for example (only) in diagnostic scenarios, or for localized ablation of discrete high-impedance nodules (such as those encountered potentially in prostate cancer tumors). For example, a two-needle array may be used to interrogate impedance between the pair, allowing CPM 800 to rapidly distinguish a fibrotic nodule from surrounding compliant tissue. In therapeutic use, alternating polarity or phase inversion protocols can be applied to the two needles, creating a highly localized bipolar current density between the opposed tips of the pair. Since the inter-electrode distance is precisely known, the thermal distribution can be highly controlled, permitting targeted collagen denaturation or micro-ablative therapy with minimal collateral spread that may be particularly useful where anatomical access is restricted, or for targeting narrow fibrotic cords or septations. Head portion 50 configuration is used in certain exemplary implementations, as a baseline tool in a modular kit, complementing larger, multi-needle arrays engineered for broader lesions.

Additionally, an interchangeable head portion 60 may be configured to feature a hybrid or asymmetric needle arrangement to address complex clinical scenarios. For example, a head portion may be designed with a central needle of a larger gauge, or having a specialized tip with microserrations, specifically adapted for mechanical disruption of dense, calcified plaques, surrounded by an array of smaller-gauge needles intended primarily for the delivery of RF thermal energy to promote collagen remodeling post-disruption. Another head portion 70 might feature an asymmetric layout of needles, clustered toward one side of distal end 212, of cap 200, for treating lesions located in anatomically challenging or constrained areas. The system's ability to independently control each $i^{th}$ needle 210*i* penetration depth and RF parameters allows for the execution of complex, multi-step treatment protocols tailored to these unique array 210*i* configurations, all under the control of CPM 800.

In an exemplary implementation, the wands, carts, and head portions disclosed herein are combined to form the kits described. Accordingly, provided herein is a kit for use in a system for ameliorating adverse side effects associated with a sub-cutaneous region exhibiting impedance that is different than surrounding tissue, the kit comprising: a wand, the wand comprising a shell and an actuator disposed within the shell; and a plurality of interchangeable head portions, each head portion configured to be reversibly, removably coupled to the wand and in communication with the actuator, each head portion comprising a needle array carrier, a needle array base plate, a cap defining a plurality of apertures, and a plurality of needles supported by the base plate and configured to pass through the apertures, wherein a first head portion of the plurality of interchangeable head portions comprises a first plurality of needles arranged in a first configuration, and a second head portion of the plurality of interchangeable head portions comprises a second plurality of needles arranged in a second configuration that is different from the first configuration.

It is further noted, that in the context of the disclosure, CPM 800 (see e.g., FIG. 5A), does not have to be in a single location and can be a combination of various processors distributed throughout the system, for example, on printed circuit board (PCB) 230 located within wand 10 shell 100 (see e.g., FIGS. 2, 3A, 4A, and 4B), as well is in cart 1000 (see e.g., FIGS. 5A, 5B). Additional PCBs can be used, for example in base plate 260, and in carrier 290 PCB 280 (see e.g., FIGS. 2-3B). These PCBs and microprocessors or processors can be used to control operational parameters, such as depth of penetration of each $i^{th}$ needle 210*i* to be actuated by actuator 250, polarity of each needle, signal processing in impedance measurements, RF energy intensity to each $i^{th}$ needle 210*i*, time of operation for each $i^{th}$ needle 210*i*, or another similar operational parameter.

In certain exemplary implementations, current processors, microcontrollers and/or microprocessors utilized by the system and methods described, can be ARM Cortex-M series microcontrollers, such as the STM32F4 or STM32H7 families from STMicroelectronics. Additionally, or alternatively, multi-channel signal processing or complex user interface control that can be used, are, for example, NXP's i.MX series application processors, such as the i.MX 8M Mini or i.MX 7ULP, providing advanced multimedia capabilities, integrated power management, and multi-core architectures utilized e.g., in cart 1000, operable to aggregate and process data from peripheral devices, such as wand 10. Additionally, or alternatively, Texas Instruments' Sitara series (e.g., AM335x) can be used in, e.g., cart 1000 or baseplate 26, providing configuration for integrated peripherals such as analog-to-digital converters (ADCs) and PRUs (programmable real-time units) configured to handle low-latency tasks such as impedance measurement and RF modulation control.

For control needs within wand 10 or handheld unit (e.g., PCB 230 within shell 100), microcontrollers like the Nordic nRF52 series, which integrate BLE communication with a capable ARM Cortex-M4F processor, can be used, thereby providing both processing and communication.

In another exemplary implementation, actuator 250 controlling mechanical movements, such as the depth of penetration of needles (210*i*), can be, for example, linear piezoelectric actuators like Physik Instrumente (PI) or Thorlabs, configured to deliver high precision and fast response times. Alternatively, or additionally, miniature stepper motor actuators, such Faulhaber or Portescap stepper motors, can be used, configured to provide precise positioning with integrated feedback, including encoder systems for closed-loop control. In addition, RF energy delivery control can be provided using, for example digital potentiometer integrated circuits (ICs), such as Analog Devices' AD5260 or digital-to-analog converters (DACs) like Analog Devices' AD5686R can be configured to modulate RF intensity levels. These can be managed by the local microcontroller or processor on the associated PCB (e.g., 260, 280).

For controlling polarity of each needle or managing RF switching, the system used to implement the methods disclosed, can use, for example; analog switches or multiplexers such as the ADG5408 from Analog Devices, providing high voltage and low signal leakage. Additional and/or alternative components used can be, for example, specialized RF switches like those from Peregrine Semiconductor (now pSemi), e.g., PE4259, providing medical-grade RF signal routing with minimal loss and high isolation, which are beneficial in the amelioration of side effects associated with PD.

In yet another exemplary implementation, signal processing for measuring, e.g., impedance the systems used to implement the methods disclosed can implement integrated impedance converters like the Analog Devices AD5933, providing frequency sweeping and impedance data acquisition. Alternatively, and/or additionally, precision ADCs such as the Texas Instruments ADS1299 can be used, optionally, operably coupled to digital signal processing (DSP)-enabled microcontrollers like the STM32F7 series configured process data locally, before data transmission to CPM 800

In an exemplary implementation, system 20 further comprising cart 1000, cart 1000 comprising: housing having upper surface 1020, lower surface 1020' (not shown), front wall 1050, rear wall 1050' and pair of side walls 1040, 1040', with user interface 1010, including display 1012 coupled to upper surface 1020 of housing (see e.g., FIGS. 5A, 5B) through, for example support member 1011; first $q^{th}$ connection port 1061*q*, in communication with wand 10; and second connection port 1062 optionally in communication with RF generator 850. As illustrated, RF generator 850 can be a stand-alone unit, or can be integrated into cart 1000, together with non-transitory memory device 810.

Also illustrated in FIGS. 5A, 5B, wheel base having arms 1100 and 1110, with wheels 1101-1104 coupled thereto. Additionally, emergency stop button 1060, as well as handle 1052 and various hooks and shelves 1030, 1041-1043, with vent 1053 also shown.

While in the foregoing specification methods and systems for ameliorating focal tunical fibrosis by delivering focused energy to the focal tunical fibrosis described herein, have been described in relation to certain preferred exemplary implementations, and many details are set forth for purpose of illustration, it will be apparent to those skilled in the art that the disclosure of the systems for ameliorating focal tunical fibrosis by delivering focused energy to the focal tunical fibrosis described herein and their methods of use are susceptible to additional exemplary implementations and that certain of the details described in this specification and as are more fully delineated in the following claims can be varied considerably without departing from the basic principles of the disclosure.

What is claimed:

1. A system for use in a procedure for ameliorating adverse side effects associated with a sub-cutaneous region exhibiting impedance that is different than the surrounding tissue and/or organ in a subject in need thereof, by applying RF energy thereto, the device comprising:

a) a wand having a at least one needle adapted, sized and configured to penetrate a surface of a skin region of the subject;

b) a radio frequency (RF) generator, arranged to deliver RF energy to the sub-cutaneous region exhibiting impedance that is different than the surrounding tissue and/or organ via the at least one needle; and c) a central processing module (CPM), in communication with the wand, and the RF generator, the CPM further comprises at least one processor in communication with a non-transitory memory device, storing thereon a computer-readable media with a set of executable instructions configured, when executed by the at least one processor to:

i. control depth of penetration of the at least one needle;

ii. control an intensity of an RF energy delivery by the RF generator to the sub-cutaneous region exhibiting impedance that is different than the surrounding tissue and/or organ;

iii. selectably control penetration depth of each needle in an array of the plurality of needles;

iv. detect electrical impedance measured in each needle in the array of the plurality of needles penetrated to the area beneath the penetrated skin; and v. dynamically assign polarity to each needle of the plurality of needles penetrated to the area beneath the penetrated skin, based on the detected impedance, wherein the sub-cutaneous region exhibiting impedance that is different than the surrounding tissue and/or organ, is a focal tunical fibrosis, exhibiting a higher impedance.

2. The system of claim 1, wherein the CPM is operable to cause at least one needle of the plurality of needles to penetrate between 0.1 mm and 10 mm into the focal tunical fibrosis.

3. The system of claim 1, wherein each needle of the plurality of needles are sized and configured to penetrate the surface of the user's skin adjacent the focal tunical fibrosis at an angle of between 0° and 90° off horizontal.

4. The system of claim 3, wherein the plurality of needles comprises between two and 36 needles.

5. The system of claim 4, wherein the plurality of needles are arranged in array of: plurality of rings, squares, or parallel lines each arrangement comprising at least a pair of diametrically opposed needles, and wherein each ring is rotatably coupled to the wand.

6. The system of claim 3, further comprising a user interface, wherein the set of executable instructions is further configured, when executed by the one processor to cause the CPM to:

a) identify a needle of the plurality of needles determined to have impedance associated with the focal tunical fibrosis;
b) classify the focal tunical fibrosis based on the measured impedance;
c) using the user interface, indicate a focal tunical fibrosis class;
d) based on the classification, determine an action regimen comprising:
i. determining the number of needles configured to penetrate the area beneath the penetrated skin adjacent the needle of the plurality of needles determined to have impedance associated with the focal tunical fibrosis;
ii. determine the depth of penetration of each needle of the plurality of needles configured to penetrate the area beneath the penetrated skin adjacent the needle of the plurality of needles determined to have impedance associated with the focal tunical fibrosis;
iii. assign the polarity of each needle of the plurality of needles configured to penetrate the area beneath the penetrated skin adjacent the needle of the plurality of needles determined to have impedance associated with the focal tunical fibrosis;
iv. determine an RF intensity delivered to each needle of the plurality of needles configured to penetrate the area beneath the penetrated skin adjacent the needle of the plurality of needles determined to have impedance associated with the focal tunical fibrosis; and
e) execute the action regimen.

7. The system of claim 6, wherein the polarity of the needle of the plurality of needles determined to have impedance associated with the focal tunical fibrosis is different than the polarity of the plurality of needles determined not to have impedance associated with the focal tunical fibrosis.

8. The system of claim 1, wherein each needle of the plurality of needles is adapted, sized and configured to physically disrupt the focal tunical fibrosis.

9. The system of claim 1, wherein a first needle portion of the plurality of needles is insulated, and a second needle portion of the plurality of needles is uninsulated.

10. The system of claim 1, further comprising at least one electrode positioned (i) on the wand between adjacent needles, (ii) on a deployable substrate adjacent to a penile skin, or (iii) as conductive segments on a subset of needles, or a plurality of electrodes disposed on at least two of the forgoing locations, wherein the CPM is configured to:

a) dynamically assign anode and cathode roles to individual needles and electrodes to establish rotating multipolar RF circuits;
b) compute a tissue impedance gradient map from measurements across all active needles and electrodes; and
c) selectively modulate RF energy distribution to maintain a predetermined impedance variance and a predetermined thermal gradient.

11. The system of claim 1, wherein the wand further comprises:

a) a shell, having a proximal end operably coupled to the RF generator;
b) an actuator—disposed within the shell, in communication with the CPM, the actuator operable to selectably advance one or more needles in the array of the plurality of needles, each to depth determined by the CPM;
c) a head portion, comprising:
i. a plunger coupled to the actuator;
ii. a flanged handle ring;
iii. an insulating ring;
iv. a needle array carrier;
v. a needle array base plate; coupled to the needle array carrier; and
vi. a cap, defining a distal end, the distal end defining a plurality of apertures adapted, sized and configured to accommodate passage of the at least one needle, the cap coupled to the distal end of the shell.

12. The system of claim 11, further comprising a cart, the cart comprising:

a) a housing having an upper surface, a lower surface, a front wall, a rear wall and a pair of side walls;
b) a user interface coupled to the upper surface of the housing;
c) a first connection port, in communication with the wand; and
d) a second connection port optionally in communication with the RF generator.

13. The system of claim 1, wherein the sub-cutaneous region exhibiting impedance that is different than the surrounding tissue and/or organ, is a lipoma, exhibiting a lower impedance.

14. The system of claim 1, wherein the sub-cutaneous region exhibiting impedance that is different than the surrounding tissue and/or organ, is an abscess, exhibiting a lower impedance.

15. A method for ameliorating adverse side effects associated with a sub-cutaneous region exhibiting impedance that is different than the surrounding tissue and/or organ, in a subject in need thereof, implemented in a device comprising a wand having a plurality of needles adapted to penetrate a surface of a user's skin, a radio frequency (RF) generator, arranged to deliver RF energy to an area beneath the penetrated skin via at least one needle of the plurality of needles, and a central processing module (CPM), in communication with the wand, and the RF generator operable to control: the depth of penetration of each needle of the plurality of needles, an intensity of RF energy delivery by the RF generator to the area beneath the penetrated skin, and optionally, the polarity of each needle of the plurality of needles penetrated into the area beneath the penetrated skin, the method comprising:

a) penetrating a skin surface above sub-cutaneous region with the plurality of needles;
b) delivering radiofrequency (RF) energy via at least one needle to the sub-cutaneous region;
c) controlling, via the central processing module (CPM):
i. penetration depth of each needle;
ii. RF energy delivery parameters to the area beneath a penile skin; and
iii. Optionally, polarity assignment of each needle;
d) automatically adjusting needle penetration depth using processor-executed instructions;
e) measuring electrical impedance through each needle; and f) dynamically assigning needle polarity based on measured impedance.

16. The method of claim 15, wherein the sub-cutaneous region exhibiting impedance that is different than the surrounding tissue and/or organ, is a focal tunical fibrosis, exhibiting a higher impedance, and wherein:

a) the step of penetrating the skin surface comprises penetrating the skin surface adjacent the focal tunical fibrosis;

b) the step of delivering the RF energy via at least one needle, comprises delivering the RF energy via the at least one needle to an area beneath the penetrated penile skin; and c) using the CPM, controlling the RF energy delivery parameters to the area beneath the penile skin.

17. The method of claim 16, wherein needle penetration depth is controlled to penetration of between 0.1 mm and 13 mm into the focal tunical fibrosis.

18. The method of claim 17, performed using 4 to 36 needles of the plurality of needles, arranged concentrically.

19. The method of claim 17, further comprising:

a) identifying a needle of the plurality of needles determined to have impedance associated with the focal tunical fibrosis;

b) classifying the focal tunical fibrosis based on the measured impedance;

c) using user interface included with the device, indicating a focal tunical fibrosis class;

d) based on the classification, planning an action protocol comprising:

i. determining a number and an identity of needles configured to penetrate the area beneath the penetrated skin adjacent the needle of the plurality of needles determined to have impedance associated with the focal tunical fibrosis;

ii. determining and assigning the depth of penetration for the needle of the plurality of needles determined to have impedance associated with the focal tunical fibrosis, and of each identified needle of the plurality of needles configured to penetrate the area beneath the penetrated skin adjacent the needle of the plurality of needles determined to have impedance associated with the focal tunical fibrosis;

iii. assigning the polarity of the needle of the plurality of needles determined to have impedance associated with the focal tunical fibrosis, and of each identified needle of the plurality of needles configured to penetrate the area beneath the penetrated skin adjacent the needle of the plurality of needles determined to have impedance associated with the focal tunical fibrosis;

iv. based on the focal tunical fibrosis classification, determining an RF intensity delivered to the needle of the plurality of needles determined to have impedance associated with the focal tunical fibrosis, and of each identified needle of the plurality of needles configured to penetrate the area beneath the penetrated skin adjacent the needle of the plurality of needles determined to have impedance associated with the focal tunical fibrosis; and e) executing the action protocol.

20. The method of claim 16, wherein each needle of the plurality of needles are sized and configured to penetrate the surface of the user's skin adjacent the focal tunical fibrosis at an angle of between 0° and 90° off horizontal.

21. The method of claim 20, wherein the plurality of needles are arranged in a plurality of rings, each ring comprising at least a pair of diametrically opposed needles, and wherein each ring is rotatably coupled to the wand, the method further comprising rotating needle arrays during penetration to mechanically disrupt the focal tunical fibrosis.

22. The method of claim 15, wherein a first subset of needles is insulated and a second subset is uninsulated during energy delivery.

23. The method of claim 15, wherein the sub-cutaneous region exhibiting impedance that is different than the surrounding tissue and/or organ, is a lipoma, exhibiting a lower impedance.

24. The method of claim 15, wherein the sub-cutaneous region exhibiting impedance that is different than the surrounding tissue and/or organ, is an abscess, exhibiting a lower impedance.

* * * * *